(12) United States Patent
Ridgley et al.

(10) Patent No.: US 9,839,543 B2
(45) Date of Patent: Dec. 12, 2017

(54) MULTI-STAGE BALLOON CATHETER

(71) Applicant: Cook Incorporated, Bloomington, IN (US)

(72) Inventors: Nathan Ridgley, Bloomington, IN (US); Lindsay Koren, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 358 days.

(21) Appl. No.: 14/211,023

(22) Filed: Mar. 14, 2014

(65) Prior Publication Data

US 2014/0277351 A1 Sep. 18, 2014

Related U.S. Application Data

(60) Provisional application No. 61/784,522, filed on Mar. 14, 2013.

(51) Int. Cl.
*A61F 2/958* (2013.01)
*A61M 25/10* (2013.01)
*A61F 2/82* (2013.01)

(52) U.S. Cl.
CPC ......... *A61F 2/958* (2013.01); *A61M 25/1011* (2013.01); *A61F 2002/821* (2013.01); *A61F 2250/0039* (2013.01); *A61M 25/10185* (2013.11); *A61M 2025/1059* (2013.01); *A61M 2025/1072* (2013.01)

(58) Field of Classification Search
CPC .... A61B 17/12022; A61B 2017/22054; A61B 2017/22055; A61B 17/12027–17/12045; A61B 17/12099–17/12136; A61F 2/958; A61F 2/2433; A61M 25/10–2025/1015; A61M 25/10185; A61M 25/10186; A61M 2025/1059; A61M 2025/1072
USPC ............. 604/101.01; 606/108, 191–197, 199
See application file for complete search history.

(56) References Cited

U.S. PATENT DOCUMENTS

| 2,799,273 A | 7/1957 | Oddo |
| 3,173,418 A | 3/1965 | Baran |
| 4,648,384 A * | 3/1987 | Schmukler .......... A61M 1/3621 600/18 |

(Continued)

FOREIGN PATENT DOCUMENTS

| EP | 0 876 805 A2 | 11/1998 |
| WO | WO 99/36015 A1 | 7/1999 |

*Primary Examiner* — David C Eastwood
*Assistant Examiner* — Charles Wei
(74) *Attorney, Agent, or Firm* — Brinks Gilson & Lione

(57) ABSTRACT

A multistage balloon catheter that uses a single lumen to inflate a balloon in stages is disclosed. A fluid port provides fluid communication from an inflation lumen in the balloon catheter to the inner volume of a distal balloon. The distal balloon expands as fluid in delivered to the inner volume of the distal balloon. Once inflated, the pressure continues to rise until a threshold pressure is exceeded. A pressure sensitive inflation valve provides fluid communication into an inner volume of a second balloon disposed at least partially proximal to the distal balloon. The pressure sensitive valve allows fluid communication into the second balloon once the threshold pressure is reached in the first balloon thereby inflating the second balloon.

5 Claims, 10 Drawing Sheets

(56) References Cited

U.S. PATENT DOCUMENTS

| | | | |
|---|---|---|---|
| 5,536,252 A * | 7/1996 | Imran | A61M 25/1011 604/101.02 |
| 5,632,762 A | 5/1997 | Myler | |
| 5,733,299 A * | 3/1998 | Sheiban | A61F 2/958 604/101.05 |
| 5,749,890 A | 5/1998 | Shaknovich | |
| 5,779,673 A * | 7/1998 | Roth | A61M 35/00 604/101.03 |
| 6,254,570 B1 * | 7/2001 | Rutner | A61M 25/0017 604/101.01 |
| 6,471,672 B1 | 10/2002 | Brown et al. | |
| 6,527,692 B1 * | 3/2003 | Weinberger | A61N 5/1002 600/3 |
| 7,105,015 B2 | 9/2006 | Goshgarian | |
| 7,632,302 B2 | 12/2009 | Vreeman et al. | |
| 7,766,893 B2 | 8/2010 | Thomas | |
| 7,862,601 B2 | 1/2011 | Sanati et al. | |
| 8,197,536 B2 | 6/2012 | Krever et al. | |
| 8,398,695 B2 * | 3/2013 | Chalekian | A61F 2/856 606/192 |
| 9,034,025 B2 * | 5/2015 | Sanati | A61F 2/954 623/1.11 |
| 9,078,780 B2 * | 7/2015 | Schaeffer | A61F 2/07 |
| 9,393,027 B1 * | 7/2016 | Dooley | A61B 17/1325 |
| 2001/0023369 A1 * | 9/2001 | Chobotov | A61F 2/07 623/1.11 |
| 2003/0208183 A1 * | 11/2003 | Whalen | A61F 2/0027 604/544 |
| 2005/0055077 A1 * | 3/2005 | Marco | A61B 17/32072 623/1.11 |
| 2005/0070828 A1 * | 3/2005 | Hampson | A61F 5/012 601/152 |
| 2005/0075662 A1 * | 4/2005 | Pedersen | A61B 17/22 606/194 |
| 2005/0131446 A1 * | 6/2005 | Coughlin | A61M 25/10 606/194 |
| 2005/0177221 A1 | 8/2005 | Mustapha | |
| 2006/0058864 A1 * | 3/2006 | Schaeffer | A61F 2/07 623/1.11 |
| 2006/0258980 A1 * | 11/2006 | Bridges | A61M 25/1011 604/101.05 |
| 2007/0055358 A1 | 3/2007 | Krolik et al. | |
| 2007/0203445 A1 * | 8/2007 | Kaye | A61M 1/3653 604/6.16 |
| 2007/0219611 A1 * | 9/2007 | Krever | A61F 2/954 623/1.11 |
| 2008/0033246 A1 * | 2/2008 | Matsui | A61B 1/00082 600/115 |
| 2008/0109056 A1 * | 5/2008 | Chalekian | A61F 2/954 623/1.11 |
| 2008/0140001 A1 * | 6/2008 | Globerman | A61M 25/1011 604/97.01 |
| 2008/0208307 A1 | 8/2008 | Ben-Muvhar et al. | |
| 2008/0243233 A1 | 10/2008 | Ben-Muvhar et al. | |
| 2012/0239046 A1 * | 9/2012 | Kaiser | A61B 17/0218 606/90 |
| 2012/0245673 A1 | 9/2012 | Ma et al. | |

\* cited by examiner

MULTI-STAGE BALLOON CATHETER

RELATED APPLICATIONS

The present patent document claims the benefit of the filing date under 35 U.S.C. §119(e) of Provisional U.S. Patent Application Ser. No. 61/784,522, filed Mar. 14, 2013, which is hereby incorporated by reference.

FIELD

Embodiments of the present invention relate to methods and apparatuses for delivering an endoluminal prosthesis, such as a stent, and more particularly, to methods and apparatuses for delivering a stent into an ostium of a blood vessel or other body lumen.

BACKGROUND

Stents are an established method of treatment for conditions such as stenosis, occlusions, and other lesions within a patient's vascular system or other body lumens. An unexpanded stent is typically delivered on a catheter and expanded in place to dilate the treatment site and provide support to the lumen walls. The stent may be self-expanding, in which the stent is biased to expand when a constraint, such as when a sheath is removed. Other stents may require the use of a balloon within the stent to expand the stent.

Lesions and other conditions may occur at any location within a body lumen. In a location where a branch vessel extends from a main vessel, termed an "ostium," the branch vessel typically has a tapered section extending from the main vessel into the branch vessel. When a lesion occurs within the ostium, placement of a stent can become difficult because of the tapered section.

FIG. 1 illustrates a standard balloon catheter 100 inflated within an ostium 102 of a body lumen. The standard balloon catheter 100 is shown with a balloon 103 in an inflated state within the body lumen. The inflated state would typically be used to dilate the lumen and/or expand a stent (not illustrated). The body lumen has a tapered portion 104 in which a side branch 106 enters a main lumen 108. The balloon 103 interacts with the tapered portion 104 of the side branch 106 causing a force in a proximal direction 112 of the side branch 106. As a result, the balloon 103 may shift in the distal direction when fully inflated. This effect is dependent upon the magnitude of the taper and the length of the balloon 103 relative to the tapered portion 104. This may result in the stent being positioned in a location different from what was originally intended. It would be beneficial to deliver and expand a stent within an ostium while avoiding the "watermelon seed effect" to ensure the proper placement of the stent.

SUMMARY

In one embodiment of the invention a balloon catheter assembly comprises a catheter, a first balloon, a second balloon, a pressure actuated inflation valve, and a lumen extending from the proximal end of the catheter to the distal end of the catheter. The catheter has a proximal end and a distal end, and the first balloon is disposed at a distal portion of the catheter. The first balloon has a first interior volume. The second balloon is disposed at least partially proximal to the first balloon and has a second interior volume. The pressure actuated inflation valve is operably coupled to the second balloon and provides fluid communication through the inflation valve to the second interior volume when a threshold fluid pressure is exceeded in the first balloon. The lumen is in fluid communication with the first interior volume.

In another embodiment a method for deploying a stent using a multi-phase inflation balloon assembly comprises guiding a distal end of the catheter to a treatment site having an ostial lesion in a body lumen. Fluid is provided to the first balloon to inflate the first balloon in a non-tapered portion of the body lumen. The inflated first balloon secures the catheter within the non-tapered portion of the body lumen. Fluid is then provided to the first balloon securing the catheter until the fluid pressure in the first balloon exceeds a threshold pressure actuating the pressure actuated inflation valve. Fluid is continues to be provided to the second balloon through the pressure actuated inflation valve to inflate the second balloon thereby expanding the stent.

BRIEF DESCRIPTION OF THE DRAWINGS

To further clarify the above and other advantages and features of the one or more present inventions, reference to specific embodiments thereof are illustrated in the appended drawings. The drawings depict only typical embodiments and are therefore not to be considered limiting. One or more embodiments will be described and explained with additional specificity and detail through the use of the accompanying drawings in which.

The drawings are not necessarily to scale.

DETAILED DESCRIPTION

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Detailed Description does not contain all of the aspects and embodiments of the one or more present inventions, is not meant to be limiting or restrictive in any manner, and that the invention(s) as disclosed herein is/are and will be understood by those of ordinary skill in the art to encompass obvious improvements and modifications thereto.

Additional advantages of the present invention will become readily apparent from the following discussion, particularly when taken together with the accompanying drawings.

In the following discussion, the terms "distal" and "proximal" will be used to describe the opposing axial ends of the inventive balloon catheter, as well as the axial ends of various component features. The term "distal" is used in its conventional sense to refer to the end of the apparatus (or component thereof) that is furthest from the operator during use of the apparatus. The term "proximal" is used in its conventional sense to refer to the end of the apparatus (or component thereof) that is closest to the operator during use. For example, a catheter may have a distal end and a proximal end, with the proximal end designating the end closest to the operator heart during an operation, such as a handle, and the distal end designating an opposite end of the catheter, such as treatment tip. Similarly, the term "distally" refers to a direction that is generally away from the operator along the apparatus during use and the term "proximally" refers to a direction that is generally toward the operator along the apparatus.

Figure 2:
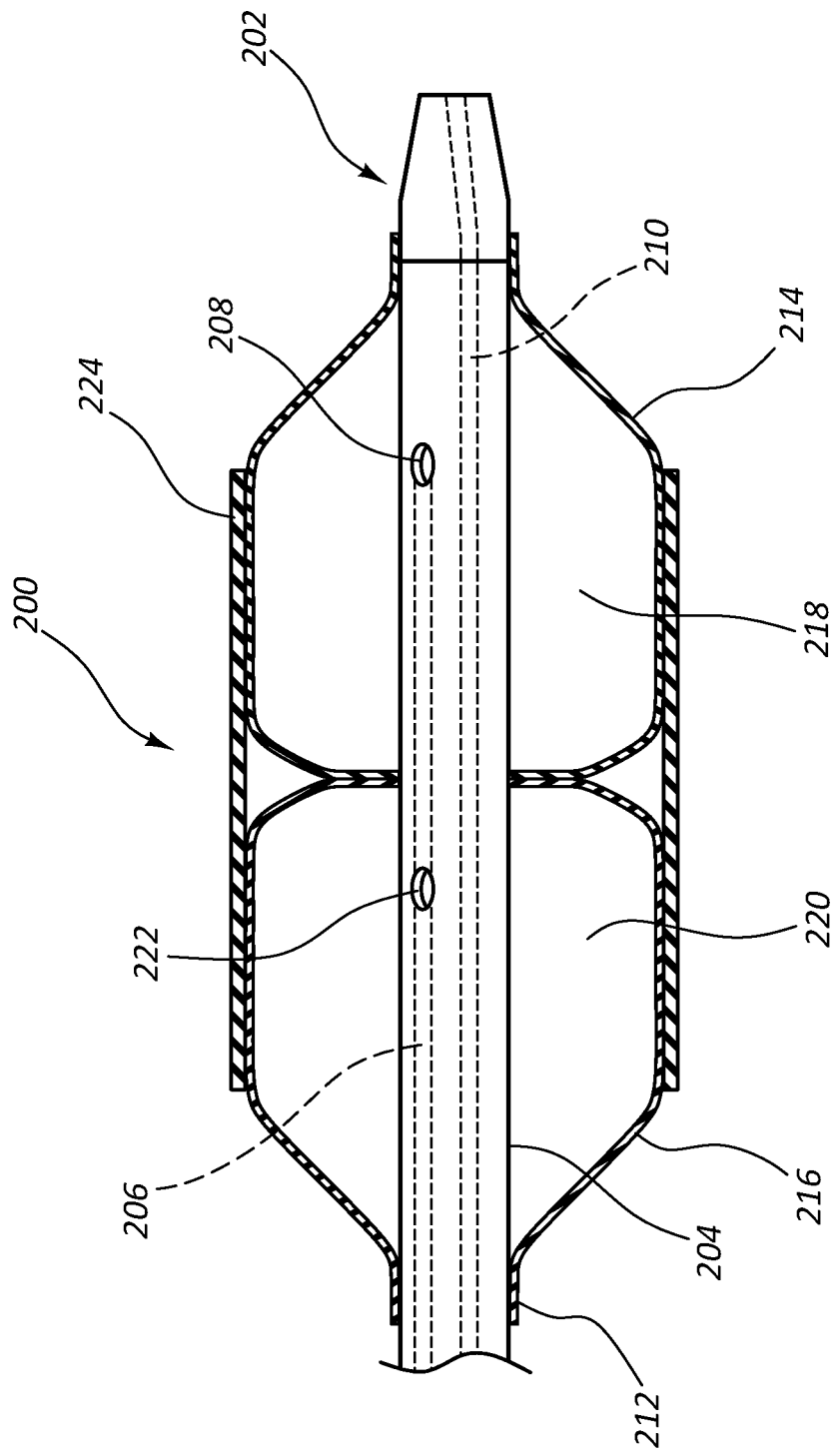
FIG. 2 illustrates an embodiment of a multistage balloon catheter for deploying a stent.

FIG. 2 illustrates an embodiment of a multi-stage balloon catheter 200 having multiple balloons inflated. The multi-stage balloon catheter 200 is comprised of a catheter body 204 having a distal end 202 and a proximal end (not shown). The proximal end would typically extend out of a patient body during use and may terminate in a hub or other typical component. The catheter body 204 has a lumen 206 for delivering inflation fluid to a first inflation port 208 and a second inflation port 222. In some embodiments, including the embodiment of FIG. 2, the catheter body 204 has an additional lumen 210 for receipt of a wire guide (not shown). The wire guide may be guided to a treatment site and then the catheter body 204 is advanced over the wire guide to position the distal end 202 of the catheter body 204 proximate the treatment site.

The first balloon 214 has a first volume 218 and the second balloon 216 has a second volume 220. Introduction of an inflation fluid into either of the volumes 218, 220 will inflate the respective balloon 214, 216 associated with that volume 216, 220. The first port 208 provides fluid communication between the lumen 206 and the first volume 218 and the second port 222 provides fluid communication between the lumen 206 and the second volume 220. A stent 224 is shown on the exterior of the balloons 214, 216 in an expanded state.

Figure 1:
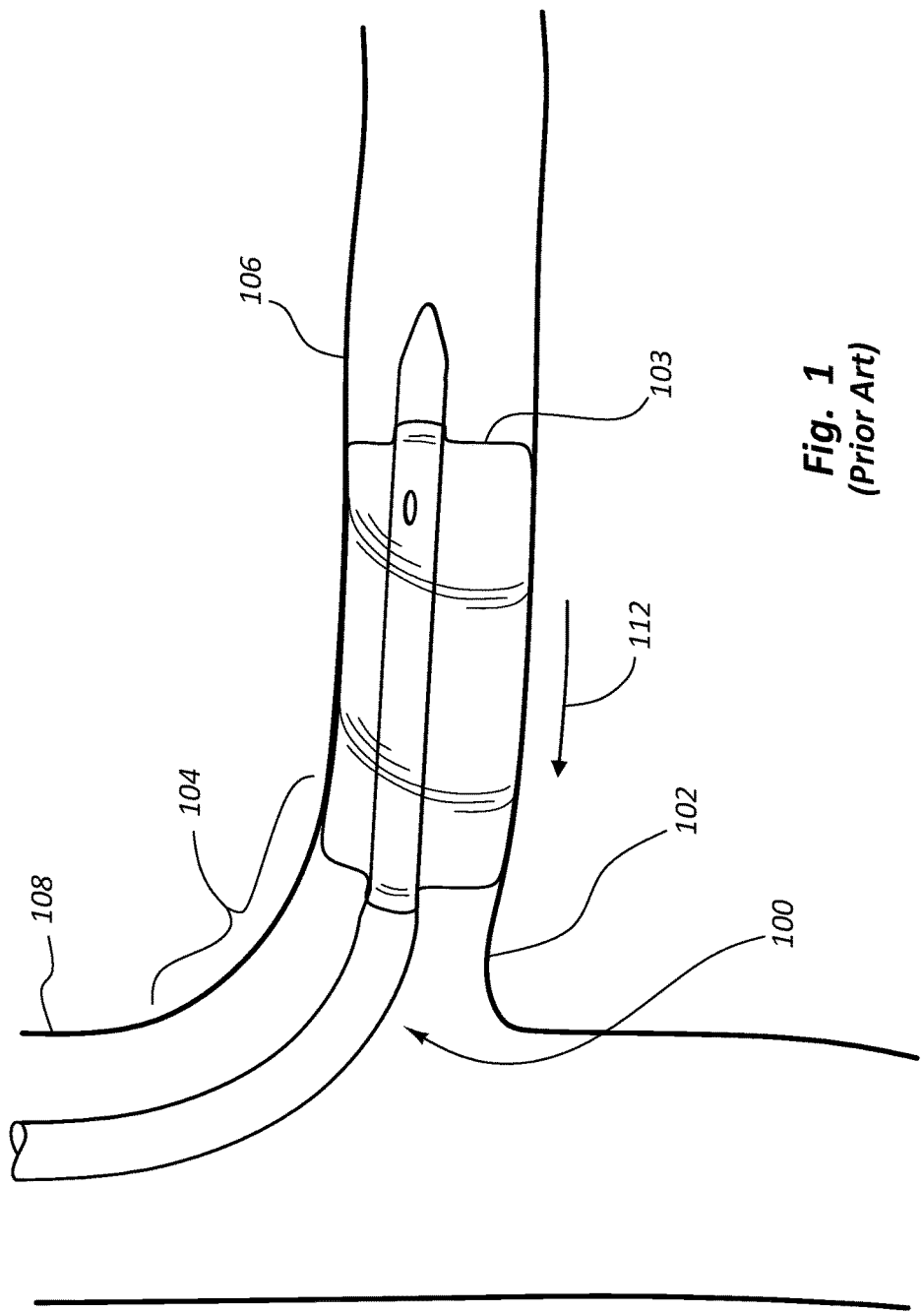
FIG. 1 illustrates a standard balloon catheter being deployed proximate an ostium of a branch vessel.
Figure 3:
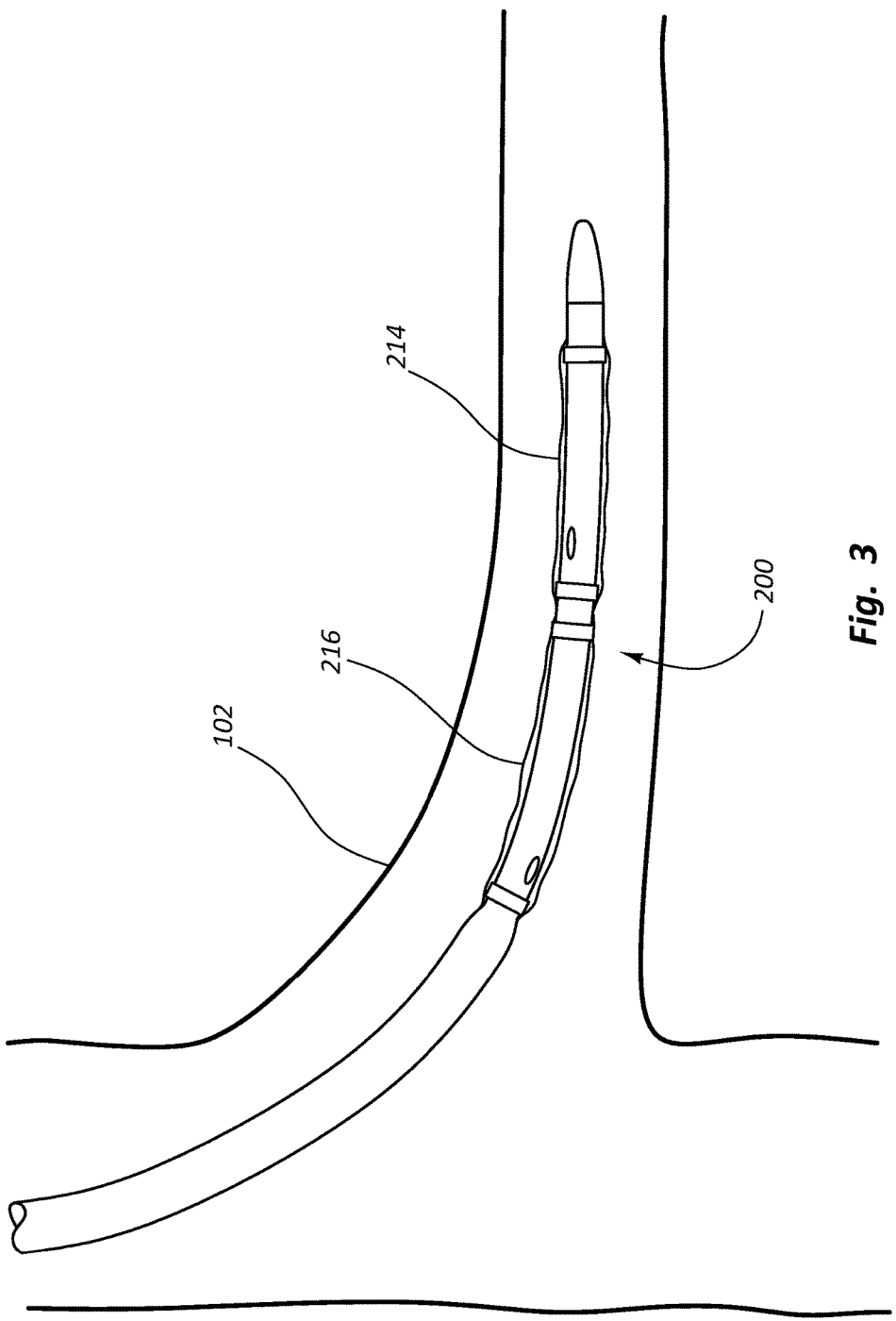
FIG. 3 illustrates the embodiment of FIG. 2 in an uninflated state.
Figure 4:
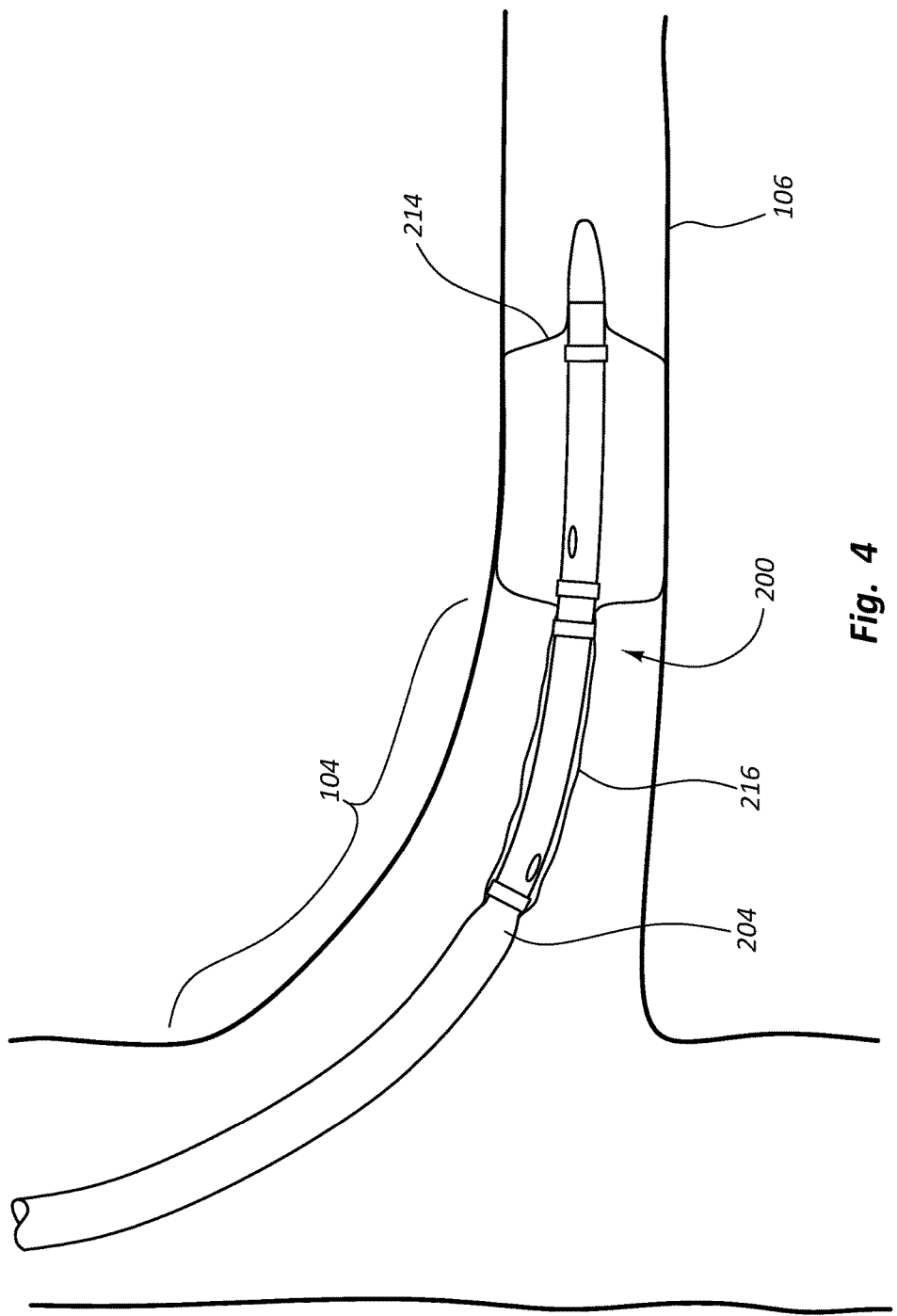
FIG. 4 illustrates the embodiment of FIG. 2 with the distal balloon being inflated to expand a distal portion of a stent prior to expanding a proximal portion of the stent.
Figure 5:
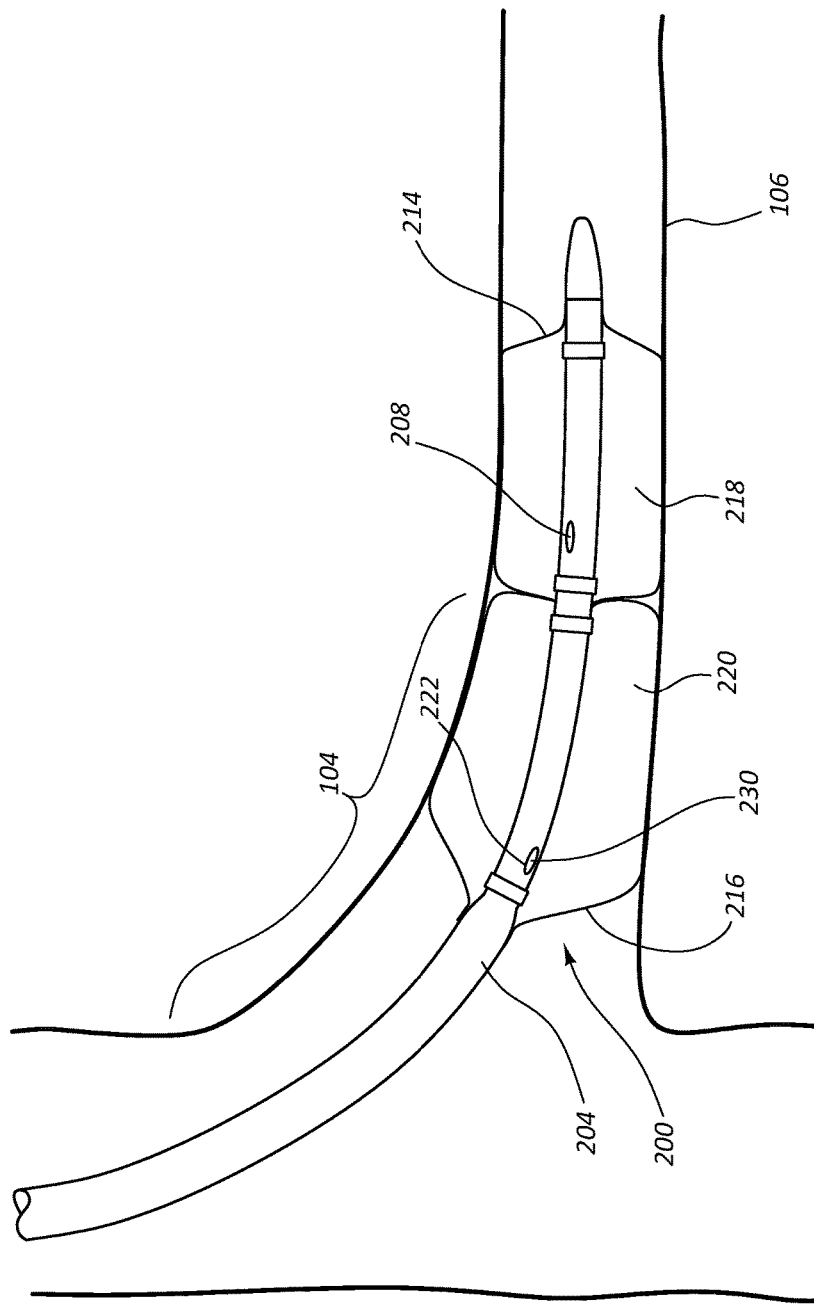
FIG. 5 illustrates the embodiment of FIG. 2 with both the proximal and distal balloons being inflated to expand a stent.

FIG. 3 through FIG. 5 illustrate the multi-stage balloon catheter 200 of FIG. 2 being inflated within the ostium 102 of FIG. 1. FIG. 3 illustrates the multi-stage balloon catheter 200 having the balloons 214, 216 in an uninflated state. In typical use, the multi-stage balloon catheter 200 would be delivered to the treatment site in such a state. The multi-stage balloon catheter 200 may have a stent (not illustrated) disposed about at least a portion of the balloons 214, 216.

FIG. 4 illustrates the multi-stage inflation balloon catheter 200 having the first balloon 214 inflated. The first balloon 214 is located generally distal to the second balloon 216 and during use inflates prior to the inflation of the second balloon 216. By inflating the distal balloon 214 first, the multi-stage balloon catheter 200 may be secured within the straight section of the branch vessel 106 prior to the second balloon 216 expanding in the tapered section 104. The first balloon 214 is inflated to a pressure sufficient to secure the multi-stage inflation catheter 200 within the branch vessel 106. Once the multi-stage inflation balloon catheter 200 is secured, the second balloon 216 inflates, expanding the stent in the tapered section 104. The second balloon 216 may expand a stent in the tapered portion 104 of the branch vessel 106. Because the first balloon 214 has already secured the multi-stage balloon catheter 200, any interaction of the second balloon 216 and the tapered portion 104 is not likely to result in any significant movement of the catheter body 204 relative to the branch vessel 106.

FIG. 5 illustrates the second balloon 216 being inflated with the first balloon 214 inflated and in place. The outer surface of the second balloon 216 takes the tapered shape of the branch vessel 106. Lateral movement of the multistage balloon catheter 200 caused by the interaction of the tapered portion 104 of the branch vessel 106 with the multistage balloon catheter 200 is minimized since the multistage balloon catheter 200 is anchored by the inflated first balloon 214 within the straight section of the branch vessel 106. In this particular embodiment, the sequence of the balloons 214, 216 inflating may be controlled using a pressure sensitive inflation valve 230 disposed in the second inflation port 222. The inflation fluid is first provided to the first volume 218 through the first port 208 until the first balloon 214 is inflated to a desired size. As the first balloon 214 inflated to secure the distal end of the stent, the fluid pressure will raise within the first volume 218. Because the inflation fluid is typically a non-compressible liquid, the pressure will increase within the lumen as well. Once the first balloon 214 has sufficiently anchored the stent, the internal pressure is increased to actuate the pressure sensitive inflation valve 230. The pressure sensitive inflation valve 230 may be a simple rupture disk that ruptures when the pressure exceeds a threshold pressure. Once the pressure sensitive inflation valve 230 opens, inflation fluid will flow through the pressure sensitive inflation valve 230 into the second volume 220, expanding the proximal end of the stent as shown in FIG. 5.

Figure 10:
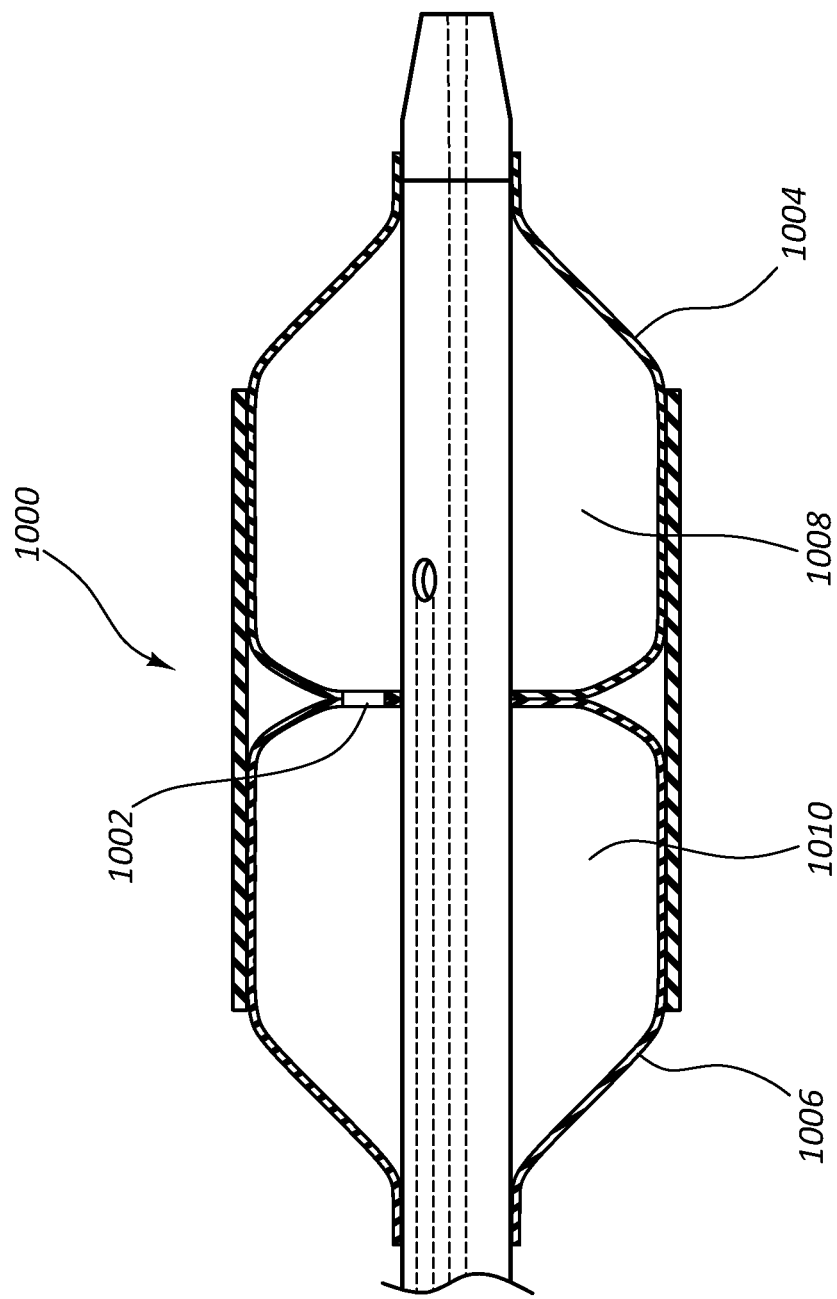
FIG. 10 illustrates another embodiment of a multistage balloon catheter for deploying a stent.

In another embodiment of a multistage balloon catheter 1000 shown in FIG. 10, a pressure sensitive inflation valve 1002 may be placed between a first balloon 1004 and a second balloon 1006. The pressure sensitive inflation valve 1002 would extend from an inner volume 1008 of the first balloon 1004 to an inner volume 1010 of the second balloon 1006. In such embodiments a second inflation port is not necessary, since the pressure sensitive inflation valve 1002 provides fluid communication between the first inner volume 1008 and the second inner volume 1006 when a threshold pressure is exceeded. In such embodiments the operator inflates the first balloon 1004 as previously described. The operator then continues to increase the pressure within the first balloon 1004 until the pressure sensitive inflation valve 1002 is activated, at which point the inflation fluid may pass from the first volume 1008 to the second volume 1010. The second balloon 1006 will then begin to inflate after the first balloon 1004.

Figure 6:
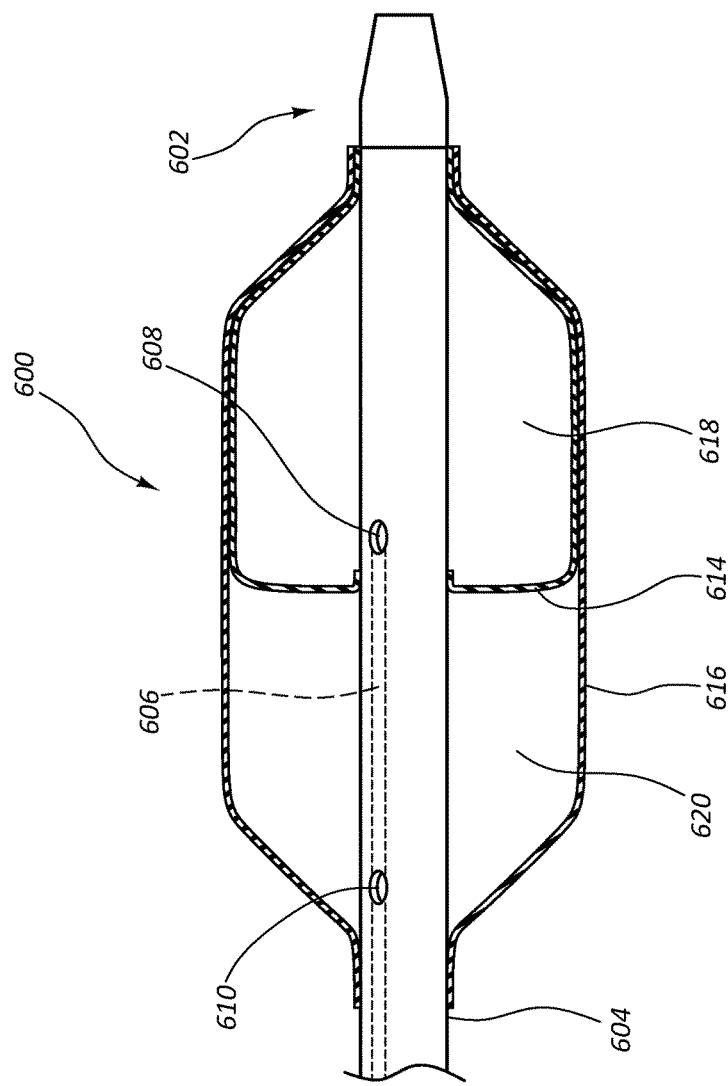
FIG. 6 illustrates another embodiment of a multistage balloon catheter for deploying a stent.

FIG. 6 illustrates another embodiment of a multi-stage balloon catheter 600 in an inflated state. The multi-stage balloon catheter 600 is comprised of a catheter body 604 having a distal end 602 and a proximal end (not shown). The proximal end would typically extend out of a patient body during use and may terminate in a hub or other typical component. The catheter body 604 has one lumen 606 for delivering inflation fluid to at least one inflation port 608. In some embodiments, including the embodiment of FIG. 6, the catheter body 204 may have an additional lumen for placement over a wire guide (not shown). The wire guide may be guided to a treatment site and then the catheter body 604 is advanced over the wire guide to position the distal end 602 of the catheter body 604 proximate the treatment site. In the embodiment of FIG. 6, the catheter body 604 has 2 inflation ports 608, 610. The first inflation port 608 provides a path for inflation fluid from the lumen 606 to a first balloon 614 and the second inflation port 610 provides a fluid path for inflation fluid to a second balloon 616 from the first lumen 606.

The distal end 602 of the catheter body 604 has a first balloon 614 and a second balloon 616 disposed thereon. The first balloon 614 has a first volume 618 and the second balloon 616 has a second volume 620. The first balloon 614 is disposed within the second volume 620. Introduction of an inflation fluid into either of the volumes 618, 620 will inflate the respective balloon 614, 616 associated with that volume 618, 620. A stent (not illustrated) may be disposed on an outer surface of the balloon 614, 616 and is expanded by the inflated balloons.

Figure 7:
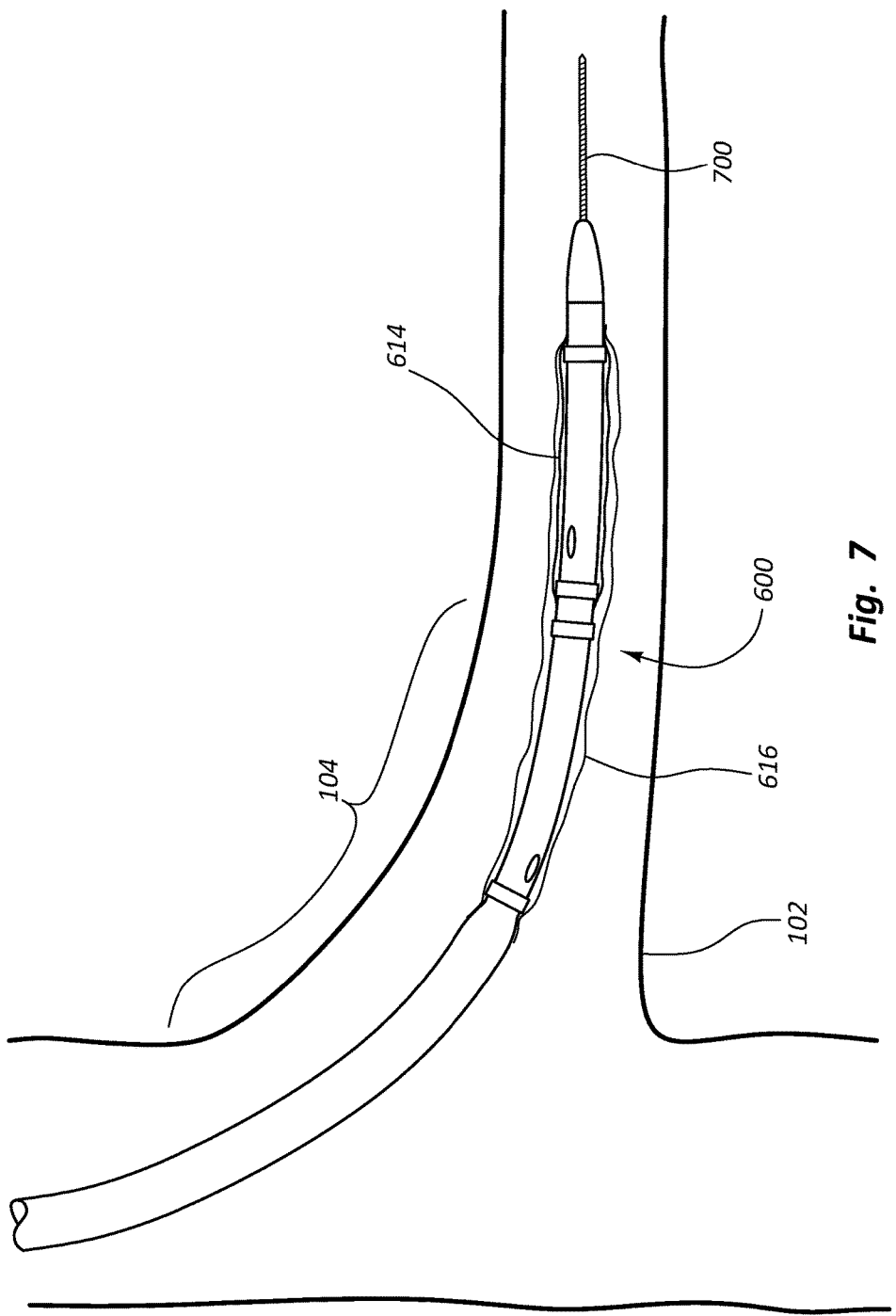
FIG. 7 illustrates the embodiment of FIG. 6 in an uninflated state.
Figure 8:
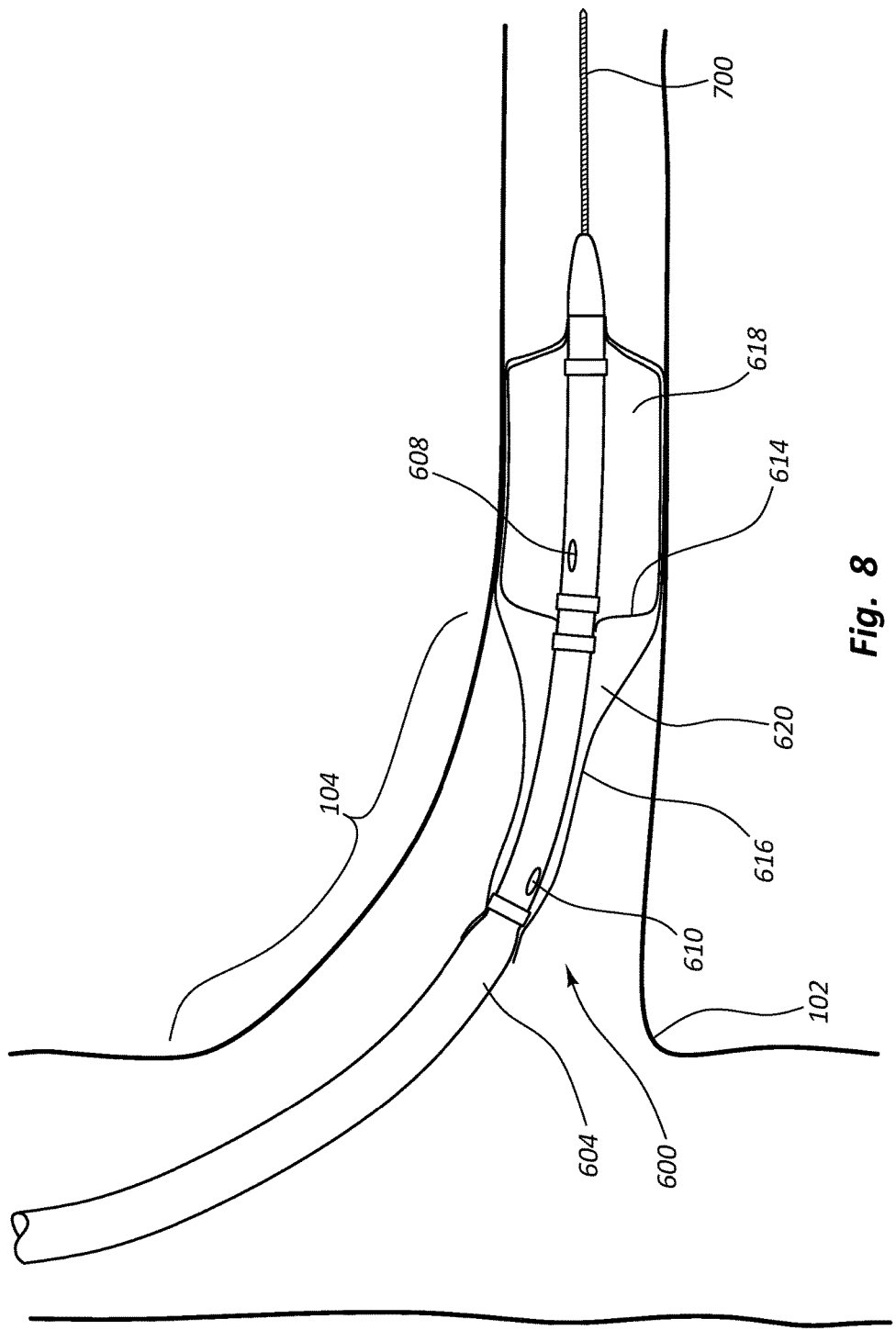
FIG. 8 illustrates the embodiment of FIG. 6 with the distal balloon being inflated.
Figure 9:
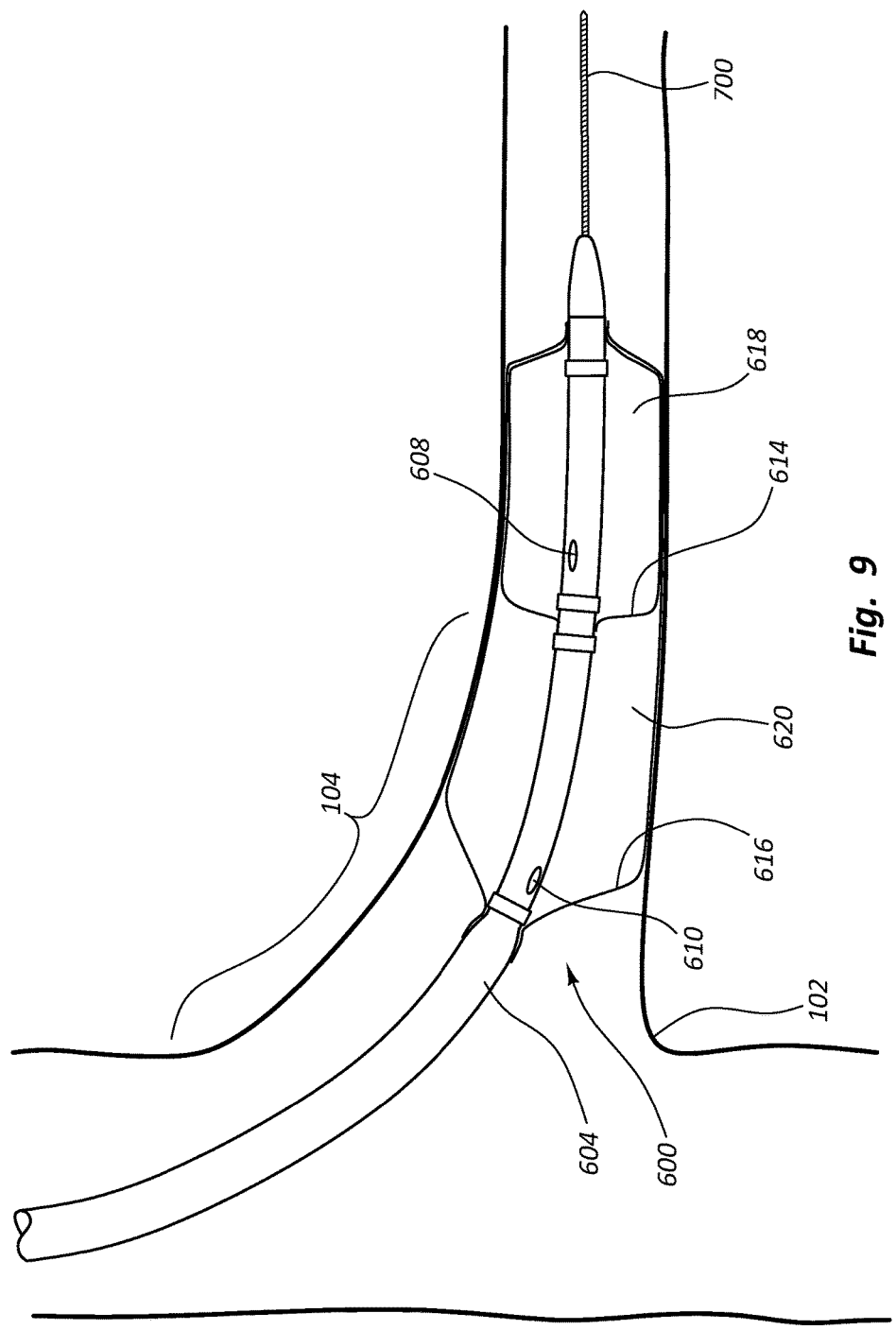
FIG. 9 illustrates the embodiment of FIG. 6 with both the proximal and distal balloons being inflated to expand a stent.

FIG. 7 through FIG. 9 illustrate an embodiment of the multi-stage balloon catheter 600 of FIG. 6 being inflated within the ostium 102 of FIG. 1. FIG. 7 illustrates the multi-stage balloon catheter 600 having the balloon s 614, 616 in an uninflated state. In typical use, a guidewire 700 is guided to a treatment site and the multi-stage balloon catheter 600 is then delivered over the wire guide 700 to the treatment site in the uninflated state of FIG. 7. The multi-stage balloon catheter 600 may have a stent (not illustrated) disposed about at least a portion of the balloons 614, 616.

FIG. 8 illustrates the multi-stage inflation balloon catheter 600 having the first balloon 614 inflated. The first balloon 614 is located within the second volume 618 and distal to at least a portion of the second balloon 616. The inflation of the first balloon 614 partially inflates the second balloon 616 since the first balloon 614 is in the second volume 618. By inflating the first balloon 614 prior to the second balloon 616, the multi-stage balloon catheter 600 may be secured within the straight section of the branch vessel 106 prior to the second balloon 616 expanding in the tapered section 104. The first balloon 614 is inflated to a pressure sufficient to secure the multi-stage inflation catheter 600 within the branch vessel 106. Once the multi-stage inflation balloon catheter 600 is secured, the second balloon 616 is expanded. The second balloon 616 may expand a stent in the tapered portion 104 of the branch vessel 106. Because the first balloon 614 has already secured the multi-stage balloon catheter 600, any interaction of the second balloon 616 and the tapered portion 104 is not likely to result in any significant movement of the catheter body 604 relative to the branch vessel 106.

The timing of the expansion of the first balloon 614 and the second balloon 616 is controlled by a pressure sensitive inflation valve in fluid communication with the second volume 620. The first port 608 provides fluid communication between the first volume 618 and the inflation lumen 606. A second port 610 provides fluid communication between the second volume 610 and the inflation lumen 606. The pressure sensitive valve inhibits the fluid from flowing from the inflation lumen 606 into the second volume 620 until a threshold pressure is exceeded. The threshold pressure is greater than a pressure necessary for the first balloon 614 to inflate and secure the multistage balloon catheter 600 within the branch vessel. In some embodiments, the second port 610 may be omitted and a pressure sensitive inflation valve may be disposed in a wall of the first balloon 614. When a threshold pressure in the first balloon 614 is exceeded, the pressure sensitive inflation valve will provide fluid communication from the first volume 618 to the second volume 620.

FIG. 9 illustrates the multistage balloon catheter 600 having both balloons 614, 616 inflated. The pressure sensitive inflation valve has actuated, allowing fluid communication between the first volume 618 and the second volume 620.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed:

1. A balloon catheter assembly comprising: a catheter having a proximal end and a distal end;
   a first balloon disposed at a distal portion of the catheter, the first balloon having a first balloon wall and a first interior volume;
   a second balloon disposed at least partially proximal to the first balloon, the second balloon having a second balloon wall and a second interior volume;
   a pressure actuated inflation valve operably coupled to the second balloon, the pressure actuated inflation valve providing fluid communication between an inflation lumen and the second interior volume through the inflation valve when a threshold fluid pressure is exceeded in the first balloon, where the pressure actuated inflation valve inhibits fluid flow through the valve below the threshold fluid pressure at which the valve permits fluid flow through the valve; and
   the inflation lumen extending from the proximal end of the catheter to the distal end of the catheter, the inflation lumen being in fluid communication with the first interior volume and the second interior volume when the threshold fluid pressure is exceeded in the first balloon so that the inflation lumen is used to inflate both the first and the second balloons;
   wherein the second balloon is inflated after the first balloon is inflated and the second balloon wall is in contact with the first balloon wall when the first and second balloons are inflated; and
   wherein the pressure actuated inflation valve is disposed between the catheter and the second balloon and passes from the lumen into the second interior space.

2. The balloon catheter assembly of claim 1 wherein the first balloon is disposed within the second interior volume.

3. The balloon catheter assembly of claim 1, wherein the pressure actuated inflation valve comprises a rupture disk.

4. The balloon catheter assembly of claim 1 wherein the catheter has only one inflation lumen.

5. The balloon catheter assembly of claim 1 wherein the first balloon is disposed within the second balloon, the pressure actuated inflation valve is covered by the second balloon when uninflated, and the threshold fluid pressure is a pressure sufficient to inflate the first balloon to a point uncovering the pressure actuated inflation valve.

* * * * *